(12) United States Patent
Soroff et al.

(10) Patent No.: US 7,641,900 B2
(45) Date of Patent: Jan. 5, 2010

(54) WOUND TREATMENT UTILIZING COLLAGENASE AND A PHOSPHOTIDYLCHOLINE ORGANOGEL

(75) Inventors: Harry Soroff, Northport, NY (US); Marcia Simon, Stony Brook, NY (US); Thomas Fallon, Saratoga Springs, NY (US); Peter Fallon, Loudonville, NY (US); Gabriele Hatch, Setauket, NY (US)

(73) Assignee: Research Foundation of State University of New York, Albany, NY (US)

( * ) Notice: Subject to any disclaimer, the term of this patent is extended or adjusted under 35 U.S.C. 154(b) by 412 days.

(21) Appl. No.: 11/093,540

(22) Filed: Mar. 30, 2005

(65) Prior Publication Data

US 2006/0222639 A1    Oct. 5, 2006

(51) Int. Cl.
*A61K 38/46* (2006.01)
*A61K 38/48* (2006.01)
*A61K 38/54* (2006.01)
*A01N 37/18* (2006.01)

(52) U.S. Cl. ............... 424/94.67; 424/94.63; 424/94.1; 514/2

(58) Field of Classification Search .... 424/94.63–94.67
See application file for complete search history.

(56) References Cited

U.S. PATENT DOCUMENTS

| | | | | |
|---|---|---|---|---|
| 5,560,910 | A * | 10/1996 | Crandall | 424/94.63 |
| 5,945,409 | A * | 8/1999 | Crandall | 514/78 |
| 6,468,551 | B1 * | 10/2002 | Diec et al. | 424/401 |
| 6,706,260 | B1 * | 3/2004 | Tanaka et al. | 424/78.06 |
| 2003/0105063 | A1 * | 6/2003 | Perricone | 514/78 |
| 2003/0170225 | A1 * | 9/2003 | Soroff et al. | 424/94.63 |
| 2005/0113731 | A1 * | 5/2005 | Qvist | 602/48 |

OTHER PUBLICATIONS

S. Demirbilek, et al., Polyunsaturated phosphatidylcholine lowers collagen deposition in a rat model of corrosive esophageal burn 2002, Eur J Pediatr Surg, 12, 8-12.*

* cited by examiner

*Primary Examiner*—Ruth A. Davis
*Assistant Examiner*—Sheridan R MaCauley
(74) *Attorney, Agent, or Firm*—Harold James; Epstein Drangel Bazerman & James, LLP

(57) ABSTRACT

The effect of the action of collagenase in treating lesions containing collagen or mixed fibrin clots (e.g., burns or ulcers) is improved by applying collagenase to the wound in combination with an organogel and a phosphatidylcholine, of which lecithin is a readily available source, particularly when the collagenase is first mixed and stored with that choline and an organic solvent and is subsequently mixed with a second individually stored formulation comprising a gel-forming agent and water, the two formulations individually having satisfactory shelf lives and the resultant mixture being applied to the lesion promptly after being formed.

14 Claims, No Drawings

WOUND TREATMENT UTILIZING COLLAGENASE AND A PHOSPHOTIDYLCHOLINE ORGANOGEL

BACKGROUND OF THE INVENTION

Collagenase has been used for years in the debridement of burns, which involve collagen, and various ulcers, which comprise mixed fibrin clots. The collagenase acts to remove the undesired tissue and thus promote the healing of the lesion. The greater the speed at which the debridement takes place the sooner will the wound heal. Thus speed of debridement is a prime consideratum.

We have discovered that if collagenase is applied to the wound in combination with a phosphatidylcholine (hereinafter termed "PC") of which lecithin is a readily available source, and an organogel a surprising increase in the speed of debridement results. Lecithin organogels have been used in the past in combination with drugs, such as non-steroidal anti-inflammatories, anesthetics, hormones, steroids and anti-histamines, in order to enable the drugs to be applied topically and readily pass through normal skin and enter the bloodstream. Debridement, however, involves treatment of tissue other than skin, and the wound-debridement effect of collagenase is significantly different from the topical or transdermal delivery of drugs to the system because entry of the collagenase into the bloodstream, to the extent that it might occur, is not a factor.

We have discovered that a combination of collagenase with an organogel including PC, such as a lecithin organogel, when applied to lesions of the type here discussed, gives rise to a surprisingly rapid debridement significantly superior to the debridement effect of other collagenase preparations. (Because of the ready availability of lecithin as a source of PC we will for the most part use the term "lecithin" to refer generically to any source of PC as well as specifically to those complex substances to which the term is normally applied.)

Institutions where burns are treated, such as hospitals and in particular burn centers where burn treatment is the rule and not the exception, must maintain on the shelf adequate supplies of collagenase, so as to be ready to treat burn cases as soon as they are presented, in order both to speed healing and minimize pain. It therefore is essential that the collagenase standing on the shelf waiting to be used should have as long a shelf life as possible. However, it is well known that certain collagenase compositions which are quite satisfactory when first prepared find their potency waning significantly with time. In particular, combinations of collagenase with water or aqueous excipients, while therapeutically highly acceptable, nevertheless have a shelf life at room temperatures of two weeks or less, which makes them unsatisfactory.

The PC (lecithin) organogels useful in the present invention may contain water. In patent application Ser. No. 10/094,226, filed Mar. 11, 2002, and titled "METHOD OF ENHANCING THE EFFECT OF COLLAGENASE ON WOUNDS" some of us have disclosed that the shelf life problem presented by aqueous collagenase mixtures, which are very effective in debridement, can be overcome by starting with a first substance comprising collagenase in a non-aqueous excipient and a separate second substance comprising an aqueous excipient, the two substances being combined at the time of application to produce an improved and surprisingly rapid treatment effect as compared with applying the collagenase to the wound in a non-aqueous excipient or in an aqueous excipient alone. The advantages of that approach to the use of collagenase are also obtainable in connection with the present invention when the collagenase is initially combined with lecithin and an organic solvent to produce a non-aqueous phase and when the gel-forming agent is initially combined with water to produce an aqueous phase, the two phases being separately stored and each having an effective shelf life, the two phases being mixed together shortly prior to application to the wound.

It therefore is the prime object of the present invention to combine collagen with a substance which enhances the collagen's normal debridement effect, and to do so through the use of readily available ingredients and in a manner which enables the components when stored to have an adequate shelf life.

DETAILED DESCRIPTION

The first, a non-aqueous phase, comprises, in addition to the collagenase, a PC, of which lecithin is a readily available source, and an organic solvent. The lecithin may be in the form of soya, but that is not essential. Other sources of lecithin are meringue tissue, hepatic tissue, cardiac tissue and egg yolks. The organic solvent is capable of dissolving lecithin and is preferably one of those solvents known to have the property of enhancing trans-dermal absorption of drugs. Preferred are ethanol, isopropyl palmitate, isopropyl myristate and ethoxy diglycol. While the relative proportions of PC and organic solvent are not critical, it has been found that approximately equal proportions by weight are quite satisfactory. A small amount of sorbic acid (0.12 g. per 6 g. of lecithin and solvent) may be added. A typical detailed composition comprises 1:1 to 0.5:5 (weight to volume) of Phosphlipon 90 (American Lecithin, Oxford, Conn.) and ethanol (1 g:1 ml). The amount of collagenase incorporated into this non-aqueous phase may vary widely, and in practice will vary depending upon the severity of the condition to be treated. 125-2500 units of collagenase per milliliter of the final combination are appropriate. 250 units per milliliter function very well. Amounts of collagenase in excess of 250 units per milliliter are not believed to be necessary when used in accordance with the present invention in view of the excellent debridement effect of 250 units, but may be called for in certain situations. If lower proportions of collagenase are employed the debridement results will be correspondingly lower but still clinically effective.

The second formulation, an aqueous phase, comprises a gel-forming agent and water. Preferred gel-forming agents are poloxamer compounds such as those sold under the trade name PLURONIC or polymers of crosslinked acrylic acid such as those sold under the trade name CARBOPOL. We have found PLURONIC F-127, which corresponds to POLAXAMO 407, a polyoxypropylene-polyoxyethylene block propolymer, to be particularly useful as a gel-forming agent. Preferred CARBOPOL resins are those which are crosslinked with polyalykeny ethers or divinyl glycol. Relative proportions of gel-forming agents and water may vary, but the combination of 10 gms of PLURONIC F-172 and 50 mls of water is quite satisfactory.

To prepare a mixture for application to the lesions, the two formulations are thoroughly mixed in relative proportions which may vary, but a combination of non-aqueous phase:aqueous phase volume relationship of 20%:80% has given excellent results. The selected volumes of the two phases are mixed by transferring appropriate amounts of each of them to individual syringes the sizes of which will depend upon the respective volumes. The two syringes are then connected to one another with a luer-to-luer lock connector and the phases are mixed by continuous transfer between the syringes, accomplished by pushing alternately on one syringe plunger and then the other. The mixture may be transferred from one syringe to the other perhaps twenty times and the shear caused by passing the mixture through the connector helps form the gel.

To demonstrate the surprising debridement effect which this procedure has, we set forth the following experimental results. For these experiments we added into each well of a six well plate an 8 ml collagen gel prepared by mixing rat tail collagen type I with DMEM, 10% fetal bovine serum, adjusting the pH to netrality and adding human fibroblasts. Phenol red was used as a pH indicator and is not an active ingredient. To initiate the experiment, small amounts (~0.5 ml) of the mixed first and second phases of the present invention mixed as described above, with a final collagenase concentration of 250 units/ml of excipient was applied to a separate gel; additional gels (placebo) with nothing added were used as controls. All of the plates were incubated for 24 hours at 37° C. The collagen gels with the placebo and with Santyl remained almost entirely intact; Santyl digested only 5-6% of the collagen. In contrast, in all five of the tests we performed the new formulation digested 34% of the collagen when mixed immediately prior to testing, representing at least a 5-6 fold increase in the activity. Again, when stored at 4° C. for 11 weeks and then tested, the new formulation digested 30% of the collagen, indicating reasonable stability.

In a report on the impact of phosphatidylcholines (PC's) on collagenase activity (digestion of collagenase), it was shown that dilinoleoyl-PC itself increases collagenase enzymatic activity two-fold whereas 2-linoleoyl-1-palmitoyl-PC is without such effect (LiJ, Kim C-I, Leo M A, et al. Polyunsaturated Lecithin Prevents Acetaldehyde=mediated Hepatic Collagen Accumulation by Stimulating Collagenase Activity in Cultured Lipocytes. Hepatology 1992; 15:373-381). A preferred organogel formulation uses soy lecithin whose major PC is dilinoleoyl-PC activation of collagenase or by the novel delivery system here disclosed. Therefore, we compared mixtures in which the non-aqueous phase comprised, in addition to collagenase and an organic solvent, either soy lecithin or 2-linoleoyl-1-palmitoyl-PC. If the dilinoleoyl-PC in the soy lecithin were responsible for the increased collagenase activity, we should have observed a lower collagenase activity using the mixture made with 2-linoleoyl-1-palmitoyl-PC. However, the formulation using 3-linoleoyl-1-palmitoyl-PC resulted in an increase in collagenase activity (70% as compared with 35%). It is therefore likely that the difference between Santyl and the new formulation is due to the collagenase-phosphatidylcholine organogel combination here disclosed.

It should be noted that although collagenase is water soluble, in accordance with the present invention it is incorporated into the first formulation, the non-aqueous formulation, in association with an organic (non-aqueous) solvent. In this way the life of the first formulation in particular is lengthened. When the two formulations are mixed the known favorable effect of water on the debridement effect of collagenase takes place, and the additional favorable debridement effect produced by the use of lecithin organogel in accordance with the present invention further enhances the wound-treatment efficacy of the combination.

While but a limited number of the embodiments of the present invention have been here specifically disclosed it will be apparent to those skilled in the art that variations may be made therein without departing from the spirit of the invention as defined in the following claims:

The invention claimed is:

1. A method for debridement of lesions containing collagen or mixed fibrin clots resulting from burns or ulcers which comprises applying to said lesion a mixture of collagenase and a phosphatidylcholine organogel.

2. A method for debridement of lesions containing collagen or mixed fibrin clots resulting from burns or ulcers which comprises applying to said lesion a mixture of collagenase and a lecithin organogel.

3. The method of claim 1, in which said phosphatidylcholine organogel comprises phosphatidylcholine, an organic solvent, water and a gel forming agent.

4. The method of claim 2, in which said lecithin organogel comprises lecithin, an organic solvent, water and a gel-forming agent.

5. The method of either of claims 3 or 4, in which said organic solvent is a member of the group consisting of organic transdermal absorption enhancers.

6. The method of either of claims 3 or 4, in which said organic solvent is a member of the group consisting of organic transdermal absorption enhancers and said gel-forming agent is a member of the group consisting of poloxamer compounds and polymers of crosslinked acrylic acid.

7. The method of claim 6, in which said organic solvent is a member of the group consisting of ethanol, isopropyl palmitate, isopropyl myristate and ethoxy diglycol.

8. The method of claim 1, in which said mixture is formed by first separately producing first and second formulations and then mixing those formulations together and applying the resultant mixture to the lesion, said first formulation being a non-aqueous phase comprising phosphatidylcholine, an organic solvent and collagenase and said second formulation being an aqueous phase comprising a gel-forming agent and water.

9. The method of claim 2, in which said mixture is formed by first separately producing first and second formulations and then mixing those formulations together and applying the resultant mixture to the lesion, said first formulation being a non-aqueous phase comprising lecithin, an organic solvent and collagenase and said second formulation being an aqueous phase comprising a gel forming agent and water.

10. The method of claim 1, in which said mixture is formed by first separately producing first and second formulations and then mixing those formulations together and applying the resultant mixture to the lesion, said first formulation being a non-aqueous phase comprising phosphatidylcholine and said organic solvent in approximately equal portions by weight and with said collagenase present in quantities of about 125 or higher units per milliliter of the final combination, said second formulation being an aqueous phase comprising said gel-forming agent and said water in approximately the proportions of 10 gms of gel-forming agent to 50 ml of water.

11. The method of claim 2, in which said mixture is formed by first separately producing first and second formulations and then mixing those formulations together and applying the resultant mixture to the lesion, said first formulation being a non-aqueous phase comprising lecithin and said organic solvent in approximately equal proportions by weight and with said collagenase present in quantities of about 125 or higher units per milliliter of the final combination, said second formulation being an aqueous phase comprising said gel-forming agent and said water in approximately the proportions of 10 gins of gel-forming agent to 50 ml of water.

12. The method of claim 10, in which said first formulation also comprises ascorbic acid and said second formulation also comprises potassium sorbate.

13. The method of claim 11, in which said first formulation also comprises ascorbic acid and said second formulation also comprises potassium sorbate.

14. The method of claim 10, in which said first formulation also comprises a small amount of potassium sorbate.

* * * * *